United States Patent
Gonzalez et al.

(12) 
(10) Patent No.: US 6,440,402 B1
(45) Date of Patent: Aug. 27, 2002

(54) PHOTOSTABLE SUNSCREEN COMPOSITIONS AND METHODS OF STABILIZING

(75) Inventors: Anthony D. Gonzalez, Waldwick; Andrew H. Pechko, Ridgewood; Robert E. Kalafsky, Ogdensburg, all of NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/020,642

(22) Filed: Dec. 14, 2001

(51) Int. Cl.[7] .............................. A61K 7/42; A61K 7/44; A61K 1/00; A61K 35/78
(52) U.S. Cl. ........................ 424/59; 424/60; 424/400; 424/401; 424/725; 424/773; 424/774; 424/775; 424/778; 424/779
(58) Field of Search .......................... 424/59, 60, 400, 424/401, 725, 773, 774, 775, 778, 779

(56) References Cited

U.S. PATENT DOCUMENTS 5,952,391 A  9/1999  Gers-Barlag et al.

FOREIGN PATENT DOCUMENTS

| JP | 61291515 A | 12/1986 |
|----|------------|---------|
| JP | 08157346 A | 6/1996  |
| JP | 09030948 A | 2/1997  |

OTHER PUBLICATIONS

"Naturally Occurring Isoamyl p–Methoxycinnamate," Langner et al., cosmetics & Toiletries Magazine, vo. 112, Jan. 1997.

*Primary Examiner*—Shelley A. Dodson
(74) *Attorney, Agent, or Firm*—Ohlandt, Greeley, Ruggiero & Perle, LLP

(57) ABSTRACT

There is provided a photostable and synergistically enhanced topical sunscreen composition. There is further provided a method of enhancing the photostability of a sunscreen active in a topical sunscreen composition. There is further still provided a method of synergistically enhancing the UV absorbance of a sunscreen active in a topical sunscreen composition. The preferred compositions and methods of the present invention use a dibenzoylmethane sunscreen active, an extract of Kaempferia Galanga, and a cosmetically acceptable vehicle.

40 Claims, No Drawings

PHOTOSTABLE SUNSCREEN COMPOSITIONS AND METHODS OF STABILIZING

BACKGROUND OF THE INVENTION

1. Field of the Invention

The present invention relates to the use of Kaempferia Galanga extract to photostabilize a topical sunscreen composition and synergistically enhance the UV absorbency of a sunscreen composition. More particularly, the present invention relates to a sunscreen composition having a sunscreen active, particularly dibenzoylmethane and/or its derivatives, and an extract of Kaempferia Galanga, particularly from the root thereof. The present invention also relates to a method of photostabilizing a sunscreen active in the topical sunscreen composition. The present invention further relates to a method of synergistically enhancing the UV absorbance of a sunscreen active in the topical sunscreen composition.

2. Description of the Prior Art

Commercial sunscreen compositions commonly employ a sunscreen active, such as a dibenzoylmethane derivative, e.g. butylmethoxydibenzoylmethane (avobenzone).

A common problem associated with some sunscreen compositions is a tendency of sunscreen actives, including dibenzoylmethane and/or derivatives thereof, to photodegrade over time from exposure to UV (ultraviolet) light. This results in an alteration of the UV absorbance of the composition and, thus, a diminution in sunscreen protection for the user during extended exposure to sunlight.

U.S. Pat. No. 5,952,391 relates to sunscreen compositions having dibenzoylmethane sunscreen actives. The compositions have flavone or flavanone derivatives to stabilize the dibenzoylmethane actives.

An extract of Kaempferia Galanga is disclosed in Naturally Occurring Isoamyl p-Methoxycinnamate, Cosmetics and Toiletries magazine, vol. 112, pp. 74–77, Jan. 1997, which is incorporated herein by reference thereto. Topical compositions having the extract are disclosed in Japanese Application Nos. 8157346A2, 61291515A2, S61-291515 and 9030948A2. The extract has been disclosed as useful as a sunscreen, anti-inflammatory agent, skin lightening agent and food ingredient.

It would be desirable to have a sunscreen composition that is photostable and affords the claimed sunscreen protection for an extended period of time. It would be further desirable to have a photostable sunscreen composition that has a dibenzoylmethane and/or derivative thereof (hereafter collectively "dibenzoylmethane"). It would be still further desirable to have a photostable sunscreen composition that affords an enhanced degree of sunscreen protection.

SUMMARY OF THE INVENTION

It is an object of the present invention to provide a topical sunscreen composition having a photostable sunscreen active.

It is another object of the present invention to provide a topical sunscreen composition affording enhanced photostability for a dibenzoylmethane sunscreen active.

It is still another object of the present invention to provide a topical sunscreen composition that exhibits synergistic UV absorbance benefits upon prolonged exposure to sunlight.

These and other objects and advantages of the present invention are achieved by a topical sunscreen composition having a sunscreen active, a photostabilizing and/or UV absorbance enhancing amount of an extract of Kaempferia Galanga, and a cosmetically acceptable vehicle.

There is also provided a method of enhancing the photostability of a sunscreen active in a topical sunscreen composition. An extract of Kaempferia Galanga is introduced into the composition in an amount sufficient to enhance the photostability of the sunscreen active.

There is also provided a method of synergistically enhancing the UV absorbance of a topical sunscreen composition having a sunscreen active. An extract of Kaempferia Galanga is introduced into the composition in an amount sufficient to synergistically enhance UV absorption.

DETAILED DESCRIPTION OF THE INVENTION

It was found surprising and unexpected that the photostability of a topical sunscreen composition having a sunscreen active, particularly dibenzoylmethane and/or derivatives thereof, could be enhanced by the introduction of an extract of Kaempferia Galanga, particularly from the root thereof. It was also found surprising and unexpected that UV absorption capability of such a composition was synergistically enhanced by the introduction into the composition of the extract of Kaempferia Galanga.

The present composition has one or more active sunscreens. Such sunscreen actives may be organic or inorganic and water-soluble or oil-soluble. Such actives include those for UVA and UVB protection (290 to 400 nanometer solar radiation). Such sunscreen actives include, but are not limited to, one or more of the following: dibenzoylmethane, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, octyl triazone, terephthalydiene dicamphor sulfonic acid, phenyl benzimidazole sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, or any derivatives or any combinations thereof. Other useful sunscreen actives include those disclosed in U.S. Pat. No. 5,000,937, which is incorporated herein by reference.

Sunscreen actives of the present invention may be present at up to about 70 percentage by weight (wt %), of the total weight of the composition. Preferably, sunscreen actives are present from about 0.05 wt % to about 50 wt %, more preferably about 0.1 wt % to about 30 wt %, and most preferably about 0.5 wt % to about 20 wt %, based on the total weight of the composition. For example, octyl methoxycinnamate is present in an amount about 2 wt % to about 10 wt %, octyl salicylate in an amount about 3 wt % to about 5 wt %, and oxybenzone in an amount about 2 wt % to about 6 wt %.

The preferred sunscreen active is dibenzoylmethane and derivatives thereof. The dibenzoylmethane sunscreen active preferably conforms to the structure:

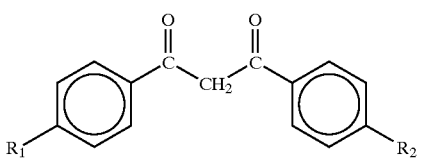

wherein $R_1$ and $R_2$ are alkyl groups having 1–36 carbons. The dibenzoylmethane sunscreen active includes, but is not limited to, butylmethoxydibenzoylmethane (avobenzone) and 4-isopropyldibenzoylmethane. The most preferred active is butylmethoxydibenzoylmethane.

The dibenzoylmethane sunscreen active is present at up to about 20 wt %, of the total weight of the composition. Preferably, the dibenzoylmethane sunscreen active is present from about 0.05 wt % to about 10 wt %, and most preferably about 0.5 wt % to about 3 wt %, based on the total weight of the composition.

The amount of sunscreen active employed will depend on the level of protection desired. Although not to be construed as limiting, compositions will typically range in level of sunscreen protection factor (SPF) from about 2 up to about 100, preferably about 2 to about 70, more preferably about 4 to about 30, and most preferably about 15 to about 30.

The present composition has an extract of Kaempferia Galanga. The extract is a crystalline solid obtained from the Kaempferia Galanga plant, also referred to as the Spice Lilly. The extract may be obtained from any part of the plant, such as the leaves, flowers, stem, bark and, most preferably, the root. The essential oil can include among its components the following: p-methoxycinnamic acid ethyl ester, p-methoxycinnamic acid methyl ester, cinnamic acid ethyl ester, n-pentadecane, 3-Carene borneol and 1,8-cineole.

The weight ratio of the extract of Kaempferia Galanga to the sunscreen active is 0.01:3 to 3:0.01. This ratio is preferably 0.01 to 0.5:1, more preferably 0.05:3, even more preferably 0.02 to 0.2:1, and most preferably 1.5:1.

Although an extract of Kaempferia Galanga is known to be useful as a sunscreen active, the effects observed in the present invention upon combination with other sunscreen actives, particularly dibenzoylmethane and/or derivatives thereof, is surprising and unexpected. First, the extract enhances or improves the photostability of the sunscreen active. The enhancement or improvement in photostability of the sunscreen active lengthens the period of time in which photoprotection by the sunscreen composition is provided. Thus, users of sunscreen compositions having the extract can be protected from sunlight for longer periods of time as compared to sunscreen compositions that do not have the extract. Second, the extract synergistically enhances or increases the level of sun protection typically provided by a sunscreen composition. In other words, the level of sunscreen protection afforded by, for example, butylmethoxy dibenzoylmethane and Kaempferia Galanga root extract is synergistically greater than the additive effect of these ingredients. This synergistic enhancement permits the use of lower levels of the sunscreen active. Thus, this effect reduces the need for reapplication. A preferred embodiment of the present invention comprises butlylmethoxy dibenzoylmethane, octyl methoxycinnamate and Kaempferia Galanga root extract.

The present composition may include any cosmetic vehicle known in the art. Suitable vehicles include, but are not limited to, one or more of the following: vegetable oils; esters such as octyl palmitate, isopropyl myristate and isopropyl palmitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; polyols such as propylene glycol, ethoxydiglycol, glycerin, butylene glycol, pentylene glycol and hexylene glycol; as well as water, or any combinations of the foregoing.

The amount of cosmetically acceptable vehicle in the present composition will vary considerably based upon product form, but typically will range from about 30 wt % to about 99.95 wt % and preferably about 50 wt % to about 99 wt %, based upon the total weight of the composition.

The present composition may take the form of an emulsion. The emulsion may be, for example, anhydrous water-in-oil, oil-in-water, water-in-silicone, or multiple emulsions. The present composition, when in emulsion form, preferably has one or more emulsifiers. Emulsifiers that can be used in the composition of the present invention include, but are not limited to, one or more of the following: sorbitan esters dimethicone copolyols; polyglyceryl-3-diisostearate; such as sorbitan monooleate and sorbitan monostearate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl-3-diisostearate; or any combinations thereof. Additional useful emulsifiers and co-emulsifiers are provided in U.S. Pat. Nos. 5,162,378 (column 4) and 5,344,665 (Table 1), which are incorporated herein by reference.

When in emulsion form, the present composition preferably has an amount of emulsifier about 0.1 wt % to about 35 wt % and most preferably about 1 wt % to about 25 wt %, based upon the total weight of the composition.

Optionally, the present composition may include one or more of the following ingredients: anesthetics, anti-allergenics, antifungals, antimicrobials, anti-inflammatories, antiseptics, chelating agents, botanical extracts, colorants, depigmenting agents, emollients, exfollients, film formers, fragrances, humectants, insect repellents (especially ethyl butylacetylaminopropionate (IR3535)), lubricants, moisturizers, pharmaceutical agents, preservatives, skin protectants, skin penetration enhancers, stabilizers, surfactants, thickeners, viscosity modifiers, vitamins, or any combinations thereof. Film formers are particularly preferred.

The present compositions may also contain one or more insect repellent actives. Such actives include, but are not limited to, N,N diethyl-m-toluamide (DEET), ethyl butylacetylaminopropionate (IR3535 by Merck Co.), hydroxyethyl isobutyl piperidine carboxylate (1-piperidine carboxylic acid) (Bayer KBR 3023), oil of citronella, soy bean oil, lemon grass oil, geranium/geraniol oil, neem oil and other natural essential oils, p-menthane-3,8-diol, or any mixtures thereof. Other useful actives are disclosed in U.S. Pat. Nos. 5,130,136 and 5,698,209, which patents are incorporated herein by reference. Preferred insect repellent actives are DEET, IR3535, p-menthane-3,8-diol and oil of citronella.

The insect repellent active is present in an amount about 0.05 wt % to about 60 wt %, and preferably about 5 wt % to about 30 wt %, based on the total weight of the composition.

Suitable film formers may include poly(vinyl pyrrolidone/1-triacontene) (Tricontonyl PVP), added at about 3 wt %.

This compound contributes film forming and water-proofing qualities to the composition. An example of such a compound is GANEX.RTM. WP 660, a film-forming water-proofing agent distributed by International Specialty Products, Co. Primarily, it is used for high quality water-proofing sunscreen formulations. Other film formers known in the art can be used advantageously in the composition. These include acrylate copolymers, acrylic $C_{12-22}$ alkyl methacrylate copolymer, acrylate/octylacrylamide copolymers, acrylate/VA copolymer, amodimethicone, AMP/acrylate copolymers, behenyl beeswax, behenyl/isostearyl, beeswax, butylated PVP, butyl ester of PVM/MA copolymers, calcium/sodium PVM/MA copolymers, dimethicone, dimethicone copolyol, dimethicone/mercaptopropyl methicone copolymer, dimethicone propylethylenediamine behenate, dimethicolnol ethylcellulose, ethylene/acrylic acid copolymer, ethylene/MA copolymer, ethylene/VA copolymer, fluoro $C_{2-8}$ alkyldimethicone, hexanediol beeswax, $C_{30-38}$ olefin/isopropyl maleate/MA copolymer, hydrogenated styrene/butadiene copolymer, hydroxyethyl ethylcellulose, isobutylene/MA copolymer, laurylmethicone copolyol, methyl methacrylate crosspolymer, methylacryloyl ethyl betaine/acrylates copolymer, microcrystalline wax, nitrocellulose, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyacrylic acid, polyethylene, polymethyl methacrylate, polypropylene, polyquaternium-10, polyquaternium-11, polyquaternium-28, polyquaternium-4, PVM/MA decadiene crosspolymer, PVM/MA copolymer, PVP, PVP/decene copolymer, PVP/eicosene copolymer, PVP/hexadecene copolymer, PVP/MA copolymer, PVP/VA copolymer, silica, silica dimethyl silylate, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, and vinyldimethicone.

The film former is present in an amount about 1 wt % to about 5 wt % of the total weight of the composition. Preferably, the film former is present in an amount about 3 wt % of the total weight of the composition.

The composition can be made into any suitable product form. Such product forms include, but are not limited to, an aerosol, balm, cream, gel, lotion, mousse, patch, pomade, pump spray, roll-on, solution, stick or towelette.

EXAMPLE

Solutions of Kaempferia Galanga extract and butyl-methoxy dibenzoyl methane (avobenzone) in diisopropyl adipate were prepared and tested for UVA absorption and photostability. Examples 1 and 2 of the present invention have a weight ratio of 1 to 1 and 0.05 to 3 (Galanga extract to avobenzone). A Control without the extract was also prepared for comparative purposes.

Photostability was measured using an Optometrics SPF 290 sold by Optometrics U.S.A., Inc. The samples were prepared using the following method:
1. Calculate the sample dosage adjusting for specific gravity;
2. Apply the sample to a substrate; and
3. Scan the sample using Optometrics SPF 290 at a predetermined site to calculate in vitro SPF measurement at that site.

The samples were then irradiated with ultraviolet light from the Optometrics SPF 290 at equivalent spectra to midday summer sunlight at 40° North latitude with a solar zenith of 20° and an ozone thickness of 0.305 cm. The ultraviolet light source is a 125 watt xenon arc lamp with sapphire window. The samples were allowed to remain exposed to the ultraviolet light at the pre-selected position. The samples were scanned every ten minutes for a total of two hours.

Overall photostability of the samples was determined by evaluating changes in the following parameters: i) critical wavelength, ii) erythemal (E) UVA PF, iii) AVG UVA PF, and iv) cumulative absorbance over the two hour period. AVG means average and PF means protection factor.

Results are set forth in Table 1.

TABLE 1

Photostability in Solution

| Parameter | Control 1 (no extract) | Example 1 (1 to 1) | Example 2 (0.05 to 3) |
|---|---|---|---|
| Δ AVG UVAPF | −91.88% | 18755.00% | 4774.00% |
| Δ E UVAPF | −87.86% | 475.00% | 677.00% |
| Δ Critical Wavelength | −1.845 | −0.61% | −0.50% |
| Δ Cumulative Absorption | −80.65% | 167.00% | 159.00% |

Δ means delta

As is evident from the results above, the change in average UVA protection factor for Examples 1 and 2 of the present invention increased 18,755% and 4,774% respectively, versus an almost 92% decline for the Control. The remainder of the data shows similarly highly surprising results. Thus, a sunscreen-containing composition having Galanga extract remains highly photostable as compared to the same composition without the extract.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method of enhancing the photostability of a sunscreen active in a topical sunscreen composition, the method comprising: introducing into the composition an amount of extract of Kaempferia Galanga plant sufficient to enhance the photostability of the sunscreen active.

2. The method of claim 1, wherein the extract of Kaempferia Galanga plant is obtained from the part of the plant selected from the group consisting of bark, flower, leaf, root, and stem.

3. The method of claim 1, wherein the extract of Kaempferia Galanga plant is obtained from a root part of the plant.

4. The method of claim 1, wherein the sunscreen active is selected from the group consisting of dibenzoylmethane, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, octyl triazone, phenyl benzimidazole sulfonic acid, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, and any derivatives thereof, and any combinations thereof.

5. The method of claim 1, wherein the sunscreen active is selected from the group consisting of dibenzoylmethane, octyl methoxycinnamate, oxybenzone, octyl salicylate, homomenthyl salicylate, and octocrylene.

6. The method of claim 1, wherein the sunscreen active is dibenzoylmethane or a derivative thereof.

7. The method of claim 6, wherein the dibenzoylmethane is butylmethoxydibenzoylmethane.

8. A method of synergistically enhancing the UV absorbance of a topical sunscreen composition comprising a sunscreen active and a cosmetically acceptable vehicle, the method comprising: introducing into the composition an amount of extract of Kaempferia Galanga plant sufficient to synergistically enhance UV absorption.

9. The method of claim 8, wherein the extract of Kaempferia Galanga plant is obtained from the part of the plant selected from the group consisting of bark, flower, leaf, root, and stem.

10. The method of claim 8, wherein the extract of Kaempferia Galanga plant is obtained from a root part of the plant.

11. The method of claim 8, wherein the sunscreen active is selected from the group consisting of dibenzoylmethane, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, phenyl benzimidazole sulfonic acid, octyl triazone, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, and any derivatives, and any combinations thereof.

12. The method of claim 8, wherein the sunscreen active is selected from the group consisting of dibenzoylmethane, octyl methoxycinnamate, oxybenzone, octyl salicylate, homomenthyl salicylate, and octocrylene.

13. The method of claim 8, wherein the sunscreen active is dibenzoylmethane or a derivative thereof.

14. The method of claim 13, wherein the dibenzoylmethane is butylmethoxydibenzoylmethane.

15. A topical sunscreen composition, comprising:
at least one sunscreen active;
an extract of Kaempferia Galanga plant; and
a cosmetically acceptable vehicle.

16. The composition of claim 15, wherein the extract of Kaempferia Galanga plant is obtained from the part of the plant selected from the group consisting of bark, flower, leaf, root, and stem.

17. The composition of claim 15, wherein the extract of Kaempferia Galanga plant is obtained from a root part of the plant.

18. The composition of claim 15, wherein the at least one sunscreen active is selected from the group consisting of dibenzoylmethane, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomenthyl salicylate, octyl dimethyl PABA, TEA salicylate, 4-methyl benzilidene camphor, octyl triazone, terephthalydiene dicamphor sulfonic acid, phenyl benzimidazole sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, and any derivatives, and any combinations thereof.

19. The composition of claim 15, wherein the sunscreen active is selected from the group consisting of dibenzoylmethane, octyl methoxycinnamate, oxybenzone, octyl salicylate, homomenthyl salicylate, and octocrylene.

20. The composition of claim 15, wherein the at least one sunscreen active is dibenzoylmethane or a derivative thereof.

21. The composition of claim 15, wherein the at least one sunscreen active is butylmethoxydibenzoylmethane.

22. The composition of claim 15, wherein the extract of Kaempferia Galanga plant is present in an amount sufficient to enhance the photostability of the sunscreen active.

23. The composition of claim 22, wherein the extract of Kaempferia Galanga plant is obtained from a root part of the plant.

24. The composition of claim 15, wherein the extract of Kaempferia Galanga plant is present in an amount sufficient to synergistically enhance UV absorbance of the composition.

25. The composition of claim 24, wherein the extract of Kaempferia Galanga plant is obtained from a root part of the plant.

26. The composition of claim 15, wherein the weight ratio of extract of Kaempferia Galanga plant to the at least one sunscreen active is about 0.01:3 to about 3:0.01.

27. The composition of claim 15, wherein the weight ratio of extract of Kaempferia Galanga plant to the at least one sunscreen active is about 0.01 to 0.05:1.

28. The composition of claim 15, wherein the weight ratio of extract of Kaempferia Galanga plant to the at least one sunscreen active is about 1.5:1.

29. The composition of claim 15, wherein the at least one sunscreen active is present up to about 70 wt % based on the total weight of the composition.

30. The composition of claim 15, wherein the at least one sunscreen active is present in an amount about 0.05 wt % to about 50 wt % based on the total weight of the composition.

31. The composition of claim 15, wherein the at least one sunscreen active is present in an amount about 0.1 wt % to about 30 wt % based on the total weight of the composition.

32. The composition of claim 15, further comprising a film former.

33. The composition of claim 32, wherein the film former is selected from the group consisting of acrylate copolymers, acrylic $C_{12-22}$ alkyl methacrylate copolymer, acrylate/octylacrylamide copolymers, acrylate/VA copolymer, amodimethicone, AMP/acrylate copolymers, behenyl beeswax, behenyl/isostearyl, beeswax, butylated PVP, butyl ester of PVM/MA copolymers, calcium/sodium PVM/MA copolymers, dimethicone, dimethicone copolyol, dimethicone/mercaptopropyl methicone copolymer, dimethicone propylethylenediamine behenate, dimethicolnol ethylcellulose, ethylene/acrylic acid copolymer, ethylene/MA copolymer, ethylene/VA copolymer, fluoro $C_{2-8}$ alkyldimethicone, hexanediol beeswax, $C_{30-38}$ olefin/isopropyl maleate/MA copolymer, hydrogenated styrene/butadiene copolymer, hydroxyethyl ethylcellulose, isobutylene/MA copolymer, laurylmethicone copolyol, methyl methacrylate crosspolymer, methylacryloyl ethyl betaine/acrylates copolymer, microcrystalline wax, nitrocellulose, octadecene/MA copolymer, octadecene/maleic anhydride copolymer, octylacrylamide/acrylate/ butylaminoethyl methacrylate copolymer, oxidized polyethylene, perfluoropolymethylisopropyl ether, polyacrylic acid, polyethylene, polymethyl methacrylate, polypropylene, polyquaternium-10, polyquaternium-11, polyquaternium-28, polyquaternium-4, PVM/MA decadiene crosspolymer, PVM/MA copolymer, PVP, PVP/decene copolymer, PVP/eicosene copolymer, PVP/hexadecene copolymer, PVP/MA copolymer, PVP/VA copolymer, silica, silica dimethyl silylate, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, vinyldimethicone, and any combinations thereof.

34. The composition of claim 32, wherein the film former is present in an amount about 1 wt % to about 5 wt % based on the total weight of the composition.

35. The composition of claim 15, further comprising an insect repellent selected from the group consisting of N,N diethyl-m-toluamide, ethyl butylacetylaminopropionate, hydroxyethyl isobutyl piperidine carboxylate, oil of citronella, soy bean oil, lemon grass oil, geranium/geraniol oil, neem oil, p-menthane-3,8-diol, and any combinations thereof.

36. The composition of claim 15, wherein the composition is in the form of a an aerosol, balm, cream, gel, lotion, mousse, patch, pomade, pump spray, roll-on, solution, stick or towelette.

37. The composition of claim 15, wherein the dibenzoylmethane sunscreen active is butylmethoxydibenzoylmethane, and the weight ratio of the extract of Kaempferia Galanga plant to the at least one sunscreen active is about 0.01:3 to about 3:0.01.

38. The composition of claim 15, wherein the dibenzoylmethane sunscreen active is butylmethoxydibenzoylmethane, and the weight ratio of the extract of Kaempferia Galanga to the at least one sunscreen active is about 0.01 to 0.5:1.

39. The composition of claim 15, wherein the dibenzoylmethane sunscreen active is butylmethoxydibenzoylmethane, and the weight ratio of the extract of Kaempferia Galanga to the at least one sunscreen active is about 1.5:1.

40. The composition of claim 15, wherein the extract is a root extract, and wherein the at least one sunscreen active is a combination of butylmethoxydibenzoylmethane and octyl methoxycinnamate.

* * * * *